(12) United States Patent
Hatch et al.

(10) Patent No.: US 6,514,415 B2
(45) Date of Patent: Feb. 4, 2003

(54) METHOD AND APPARATUS FOR MAGNETIC SEPARATION OF PARTICLES

(75) Inventors: Gareth Hatch, East Dundee, IL (US); Mike Schilling, Geneva, IL (US)

(73) Assignee: Dexter Magnetic Technologies, Inc., Fremont, CA (US)

( * ) Notice: Subject to any disclaimer, the term of this patent is extended or adjusted under 35 U.S.C. 154(b) by 0 days.

(21) Appl. No.: 09/774,825

(22) Filed: Jan. 30, 2001

(65) Prior Publication Data

US 2002/0084225 A1 Jul. 4, 2002

Related U.S. Application Data

(60) Provisional application No. 60/179,358, filed on Jan. 31, 2000.

(51) Int. Cl.⁷ .................. B01D 35/06; G01N 33/53; B03C 1/02
(52) U.S. Cl. ............ 210/695; 210/222; 209/223.1; 435/288.4; 435/305.2; 436/526; 436/809; 422/104
(58) Field of Search ............... 210/222, 695; 209/215, 223.1; 422/99, 101, 104, 186.01; 485/288.4, 305.2; 436/526, 809, 824

(56) References Cited

U.S. PATENT DOCUMENTS

| | | | |
|---|---|---|---|
| 4,438,068 A | * 3/1984 | Forrest | 436/526 |
| 4,895,650 A | 1/1990 | Wang | |
| 4,988,618 A | 1/1991 | Li et al. | |
| 5,466,574 A | 11/1995 | Liberti et al. | |
| 5,567,326 A | 10/1996 | Ekenberg et al. | |
| 5,571,481 A | * 11/1996 | Powell et al. | 209/215 |
| 5,779,907 A | 7/1998 | Yu | |
| 6,193,892 B1 | * 2/2001 | Krueger et al. | 210/695 |

* cited by examiner

*Primary Examiner*—David A. Reifsnyder
(74) *Attorney, Agent, or Firm*—Blakely Sokoloff Taylor & Zafman

(57) ABSTRACT

A method and apparatus for magnetic separation of particles within a container. In one embodiment, a container contains a number of particles and a number of magnetically susceptible particles. A number of magnets are arranged in a plane and is placed close to the container. The magnetic poles of the magnets are arranged in a pattern to apply magnetic fields oriented perpendicular to the plane on the container. The pole pattern provides in consistent separation across the container of the number of magnetically susceptible particles from the rest of the particles.

14 Claims, 9 Drawing Sheets

METHOD AND APPARATUS FOR MAGNETIC SEPARATION OF PARTICLES

This U.S. Patent application claims the benefit of U.S. Provisional Application No. 60/179,358, filed Jan. 31, 2000.

FIELD OF INVENTION

The present invention relates to the field of magnetic separation of particles in a solution. More specifically, the present invention relates to an arrangement of magnets for separating particles in a solution.

BACKGROUND OF THE INVENTION

Biological laboratories often require a technique to separate particles in a solution. Target particles, such as proteins and the like, are separated from a solution by a technique known as magnetic separation.

In general, the case of molecular biological magnetic separation of biological particles, such as target proteins, involves coating small paramagnetic materials, such as micro-beads ranging in size from a few hundred nanometers to tens of micrometers, with a chemical-specific substance that is known to chemically bond with the target proteins. The coated micro-beads are introduced into a well containing a solution of the target proteins and unwanted biological molecules. The target proteins chemically bond to the coating of the micro-beads. Magnets are placed close enough to the well to apply magnetic fields on the well and the solution.

The paramagnetic micro-beads, including the target proteins chemically bonded to the coating of the micro-beads, are attracted to the magnets in accord with the direction of the magnetic fields the magnets generate. Placement of the magnets determines where the micro-beads with the target proteins will collect, i.e., if the magnets are placed along the side of the well, the micro-beads will collect to the side wall of the well. Once the micro-beads have been collected to the desired location, the well is rinsed, removing the solution. The collected micro-beads with the target proteins chemically bonded to the coating of the micro-beads remain in the well as long as the magnetic fields are continually applied.

Once the well has been rinsed, a "clean" solution, without unwanted particles, is placed into the well. A chemical is introduced into the "clean" solution to break the chemical bonds of the target proteins and the coating of the micro-beads, resulting in a well with isolated target proteins. Additionally, the micro-beads may be removed by no longer applying the magnetic fields to the well.

Molecular biological magnetic separation is well known, and until relatively recently, this process was performed using large tubes of fluids (15–50 ml tubes) and micro-beads. Recent molecular magnetic separation techniques typically involve the use of 96-well micro-plates, that is, a tray having 96 wells, arranged in and 8×12 matrix, with each well capable of holding 250–500 micro-liter ($\mu$l) of liquid. A variety of placement methods for magnets to apply the desired magnetic fields can be employed on these micro-plates. One method is to place small magnets, having predetermined magnetic fields, between micro-plate receiving orifices, so that the micro-beads collect along the walls of the wells as described by Li, et al., U.S. Pat. No. 4,988,618. Another method is to place an apparatus with magnetic pins into the wells with the micro-beads collecting on the pins as described by Ekenberg, et. al., U.S. Pat. No. 5,567,326. Another method is to have a base for a micro-plate with cylindrical magnets positioned for insertion from the base of the micro-plate into the spaces between the wells of the micro-plate with the micro-beads collecting along the walls of the wells as described by Yu, U.S. Pat. No. 5,779,907.

As molecular magnetic separation techniques advance, the number of wells increase, and therefore, in high throughput applications, typically in automated systems, 384-well micro-plates and 1536-well micro-plates are utilized. Each 384-well micro-plate is arranged as 16×24 wells, and each 1536-well micro-plate is arranged as 32×48 wells effectively increasing the volume of the 96-well micro-plates by 4 and 16 times respectively.

The spaces between the individual wells in the 384-well and 1536-well micro-plates are relatively very small; making the magnetic separation methods of Li, Ekenberg, and Yi difficult, if not impracticable. However, magnets are still required to separate the target particles from the solution for the high throughput 384-well and 1536-well micro-plates. Also, due to the increased density of the wells, if magnetic fields are applied from areas outside of the micro-plate, the separation of particles becomes inconsistent across the micro-plates because some of the wells experience a larger magnetic field than other wells.

SUMMARY OF THE INVENTION

Disclosed is an improved arrangement of magnets for consistent magnetic separation of particles across a container, such as in the case of molecular biological magnetic separation of biological particles of the type described above. Due to the arrangement of the magnets, in particular, poles of the magnets, particles in a solution in the container are magnetically separated consistently across the container. The arrangement of the magnets allow for magnetic separation within a wide range of containers, such as micro-plates with increasing density of wells.

BRIEF DESCRIPTION OF THE DRAWINGS

The present invention is illustrated by way of example and not by way of limitation in the figures of the accompanying drawings, in which the like references indicate similar elements and in which.

DETAILED DESCRIPTION OF THE INVENTION

In the following description, various aspects of the present invention will be described. However, it will be apparent to those skilled in the art that the present invention may be practiced with only some or all aspects of the present invention. For purposes of explanation, specific numbers, materials and configurations are set forth in order to provide a thorough understanding of the present invention. However, it will also be apparent to one skilled in the art that the present invention may be practiced without the specific details. In other instances, well known features are omitted or simplified in order not to obscure the present invention.

Various operations will be described as multiple discrete steps in turn, in a manner that is most helpful in understanding the present invention. However, the order of description should not be construed as to imply that these operations are necessarily order dependent. In particular, these operations need not be performed in the order of presentation.

Figure 1:
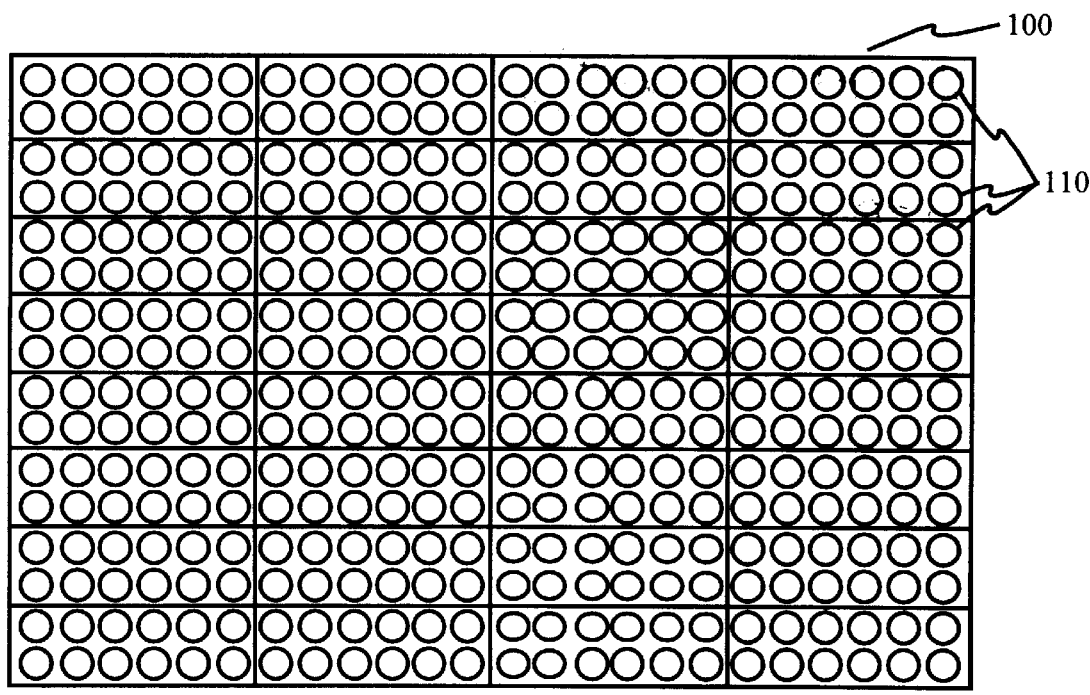
FIG. 1 illustrates a micro-plate upon which the invention may be practiced.

FIG. 1 illustrates a micro-plate upon which the invention may be practiced. FIG. 1 is a top view of a "next generation" 384-well micro-plate 100 having wells 110 arranged in a 16×24 configuration. Each of the wells 110 is capable of holding 250–500 µl of liquid. Although the wells illustrated are round, other geometric shapes are contemplated, for example, square wells may be utilized. In FIG. 1, a 384-well micro-plate is shown, however, it should be appreciated by one skilled in the art that the present invention may be practiced upon a wide range of containers used for magnetic separation of materials such as, but not limited to, 96-well micro-plates, 1536-well micro-plates, tubes, Petri dishes, and bottles.

Figure 2:
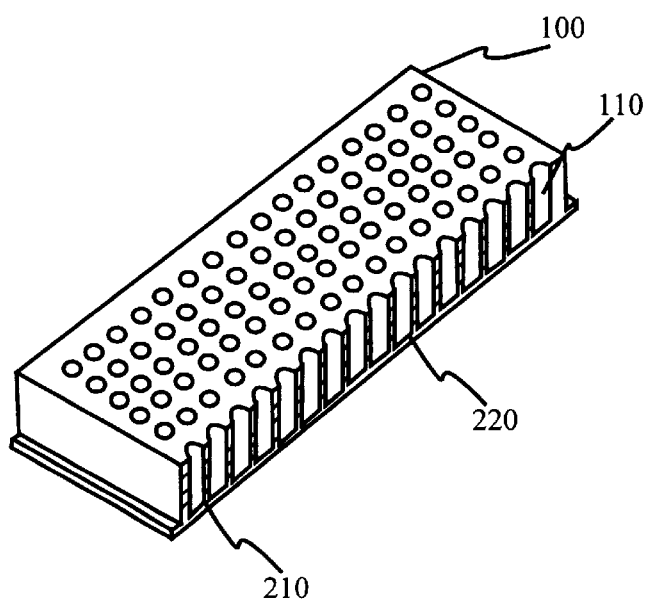
FIG. 2 illustrates a cross-sectional view of the 384-well micro-plate.

FIG. 2 illustrates a cross-sectional view of the 384-well micro-plate 100. As shown in FIG. 2, because of tightly packed density of wells, variations in separation of particles across the entire micro-plate 100 may occur. Additionally, spaces 210 between the wells 110 may be very small making placement of magnets between the wells difficult if not impracticable, and therefore, the working surface upon which the invention may be practiced is proximate the micro-plate, such as, but not limited to, the bottom surface 220 of the wells.

Figure 3:
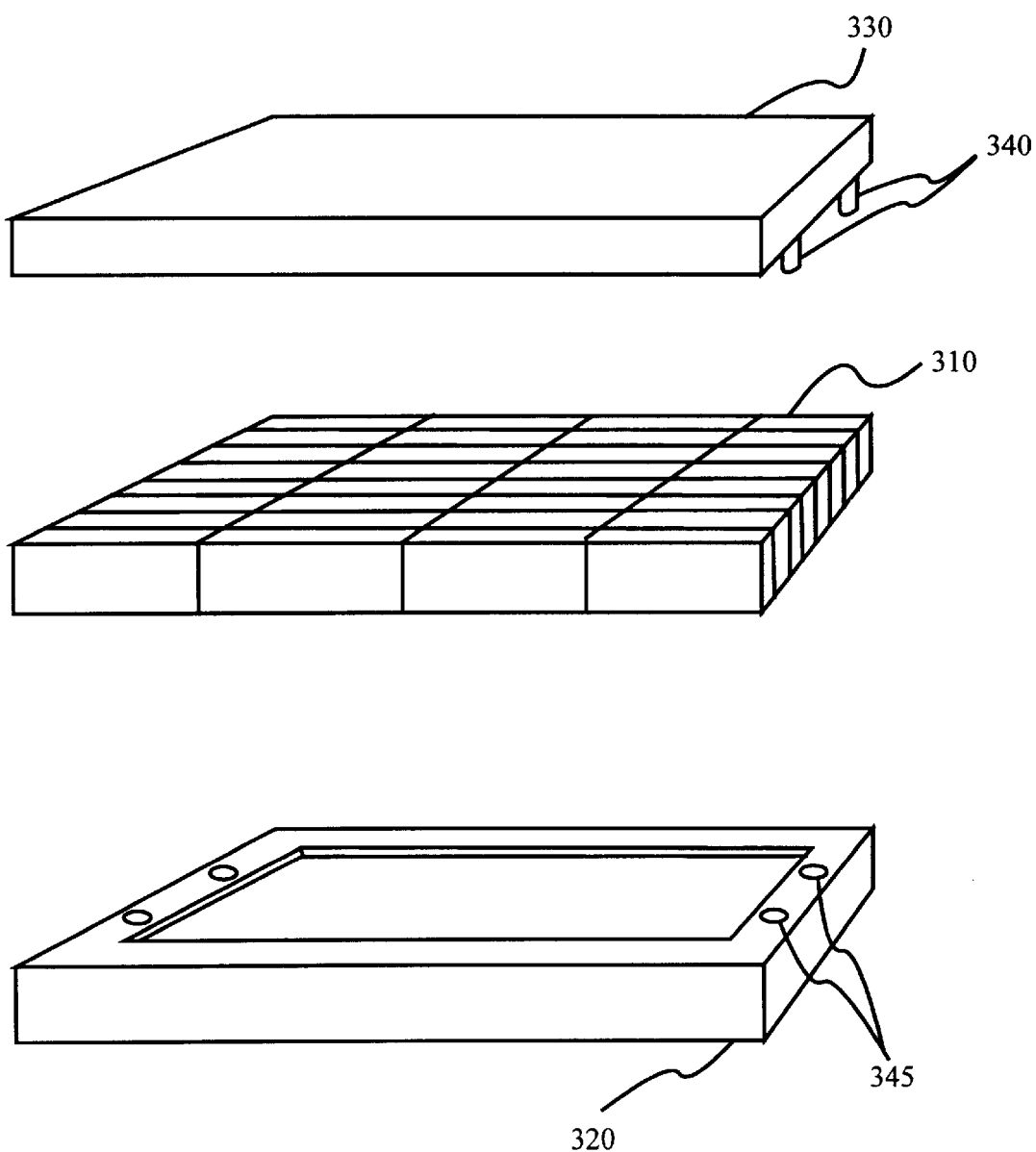
FIG. 3 illustrates one embodiment for an improved arrangement of magnets facilitating consistent separation of particles across a container.

FIG. 3 illustrates one embodiment for an improved arrangement of magnets facilitating consistent separation of particles across a container. In FIG. 3, a number of magnets 310 are encased between a cover 330 and a tray 320 applying a magnetic field to a container such as, but not limited to, the 348-well micro-plate 100 (shown in FIG. 1). The cover 330, the magnets 310, and the tray 320 may be assembled as a support plate for the container. Also shown in FIG. 3, the cover 330 includes locating pins 340, and the tray 320 includes locating pin receivers 345.

In the one embodiment shown in FIG. 3, the locating pins 340 and the locating pin receivers 345 are utilized to align the cover 330 with the tray 320. Additionally, it should be appreciated by one skilled in the art that the combination of the locating pins 340 and the locating pin receivers 345 may be utilized between the cover 330 and the micro-plate 100 (shown in FIG. 1) to align the micro-plate 100 with the cover 330. It should be appreciated by one skilled in the art that the tray 320 and the cover 330 may be of any type of material utilized for support plate covers and trays known in the art, for example, clear plastic. In one embodiment, the arranged magnets are not encased.

The magnets 310 shown in FIG. 3 are bar magnets, however it should be appreciated by one skilled in the art that the magnets 310 may be of any type of external magnetic field-producing device such as, but not limited to, wires with an electric current. Additionally, the magnets 310 may be made of materials for permanent magnets known in the art such as, but not limited to, ferromagnetic, ferrimagnetic, Alinco, polymer-bonded, rare earth, and ceramic materials. In one embodiment, these magnets may have a protective cladding. In one embodiment, these magnets may have a steel plate (not shown), between the tray 320 and the magnets 310, to shield the magnets from other fields that may interfere with the magnetic fields of the magnets. It is appreciated that the pole pattern created by the magnets, rather then the type or shape of magnets, is the focus of the present invention.

Figure 4:
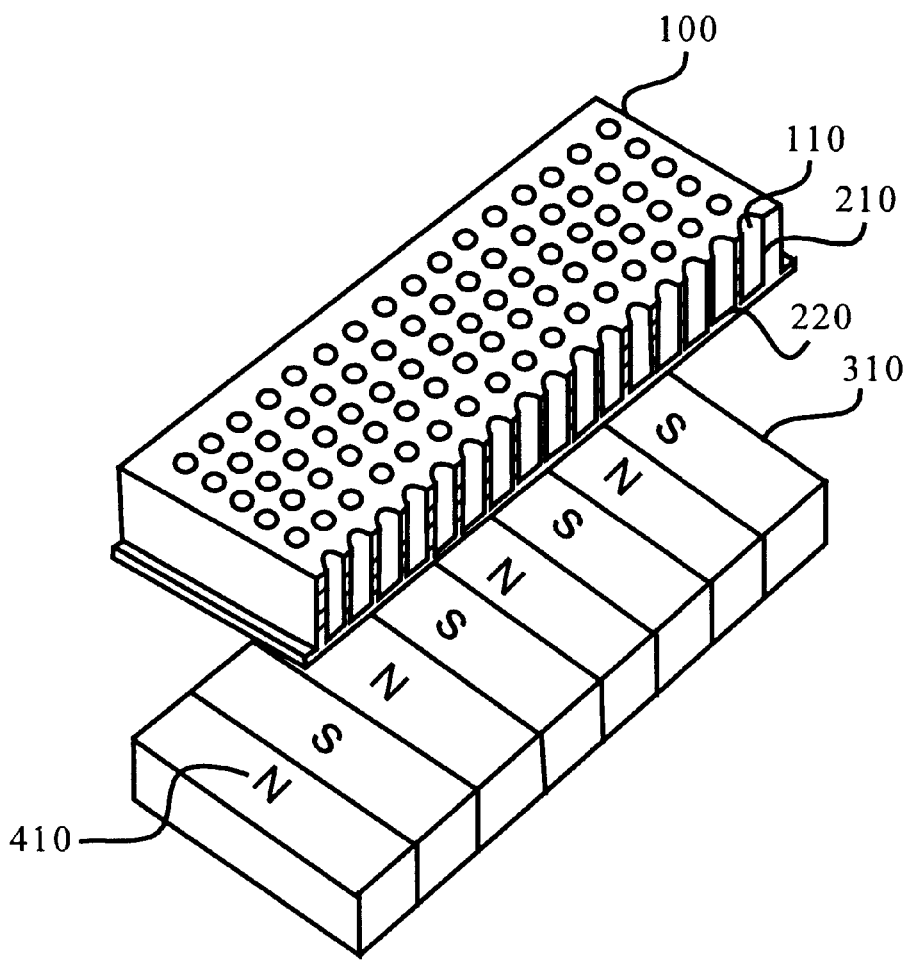
FIG. 4 illustrates a cross-sectional view of one embodiment of the invention for an improved arrangement of magnets facilitating consistent separation of particles across a container as applied to a multi-well micro-plate container.

FIG. 4 illustrates a cross-sectional view of one embodiment of the invention for an improved arrangement of magnets facilitating consistent separation of particles across a container as applied to a multi-well micro-plate container. It should be appreciated by one skilled in the art that the cross-section of the container is shown for the purposes of illustration, and the cross-section may be considered to be one half of the full container. In one embodiment, the container is the 384-well micro-plate 100 (as shown in FIG. 1) with the magnets 310 disposed below the container. As shown in FIG. 4, the 384-well micro-plate is on the top surface of the magnets 310, but it should be appreciated by one skilled in the art that the magnets 310, in particular poles 410 of the magnets 310, may be proximate the container such as, but not limited to, the side of the container. The magnets are arranged in a plane with the poles 410 of the magnets 310 corresponding to a number of wells 110 in accordance with the invention. The poles 410, shown in FIG. 4, are negative and positive magnetic poles commonly known as north (N) and south (S).

As will be described in further detail below, the result of the improved arrangement of magnets, in particular the pole pattern, poles of the magnets, in a plane, corresponding to a number of wells, facilitate consistent separation of particles across a container.

Figure 5A:
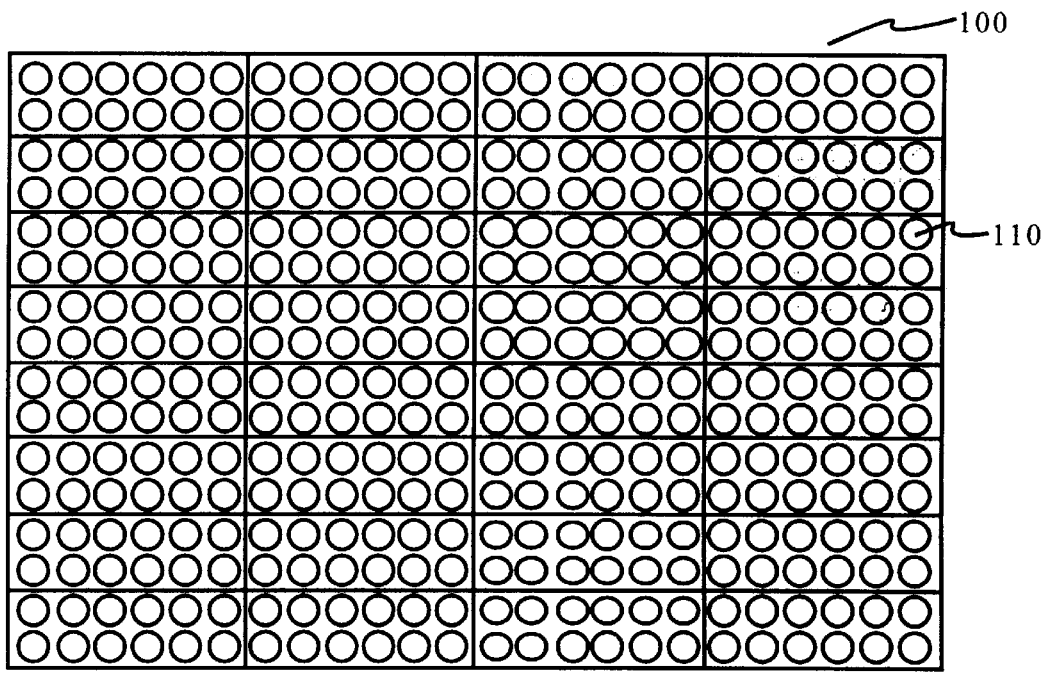
FIGS. 5a and 5b illustrate one embodiment in which an improved arrangement of magnets, in a plane with alternating poles and proximate a container, applies magnetic fields to facilitate consistent separation of particles across the container.
Figure 5B:
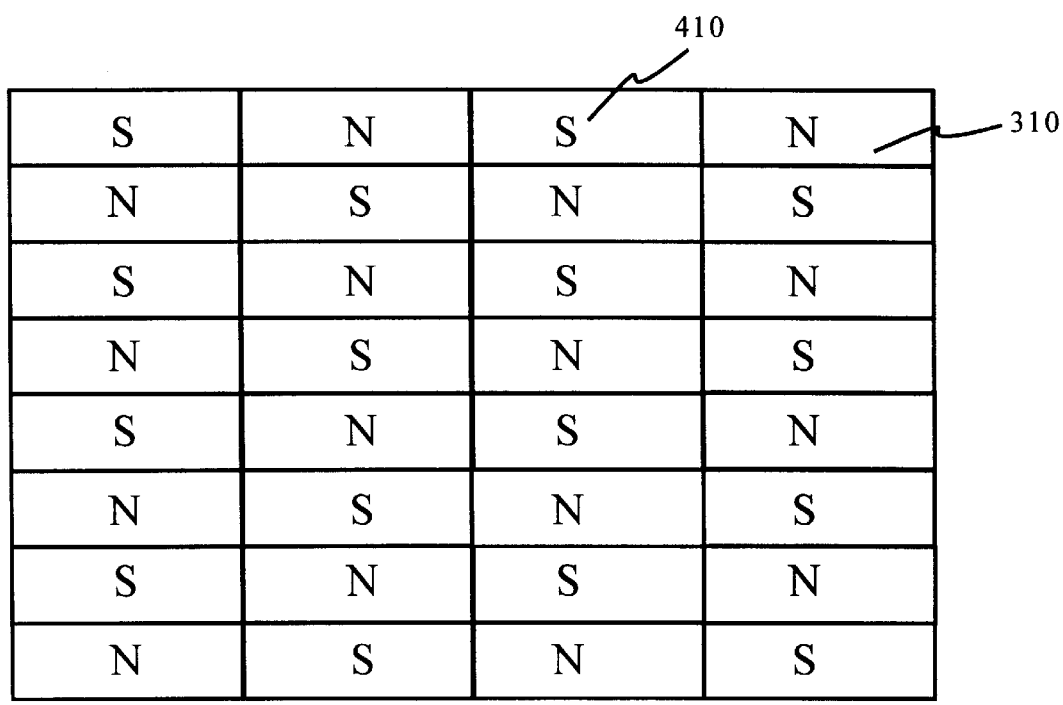

FIGS. 5a and 5b illustrate one embodiment in which an improved arrangement of magnets, in a plane with alternating poles and proximate a container, applies magnetic fields to facilitate consistent separation of particles across the container. As shown in FIG. 5a, the container is a 384-well microplate 100 with the wells 110 arranged in 16×24 matrix. As with the other wells illustrated in FIGS. 1, 2 & 4, it is appreciated that the wells ay be formed of geometric shapes other than circular, e.g., square. Shown in FIG. 5b is one embodiment of the arrangement of the magnets 310 in a plane with the poles 410 of the magnets arranged in an alternating repeat pattern in accordance with the invention. The arrangement of the poles 410 applies magnetic fields oriented perpendicular to the plane.

In one embodiment shown in FIGS. 5a and 5b, in order to apply external magnetic fields from the magnets 310 on the container 100 facilitating consistent separation of particles across the container 100, a relationship between the number of poles 410 and the number of wells 110 may be applied. In one embodiment, the relationship between the number of poles 410 and the number of wells 110 may be defined by the following relationship:

$$\text{number of wells} = A \times \text{number of poles}, \quad \text{(Rel. 1)}$$

where the A is a positive integer. The relationship will depend on the type of container, for example, for a 96-well micro-plate, the planar arrangement of magnets may be 3×1 wells per pole, for a 384-well micro-plate, the planar arrangement of magnets may be 6×2 wells per pole (as shown in FIGS. 5a and 5b), and for a 1536-well micro-plate, the planar arrangement of magnets may be 12×4 wells per pole in accordance with the invention. As a result, shown in FIG. 5, the improved arrangement of magnets 310 with the alternating pattern of poles 410 applies magnetic fields on the 384-well micro-plate 100 to magnetically separate particles consistently across the 384-well micro-plate 100.

Figure 6A:
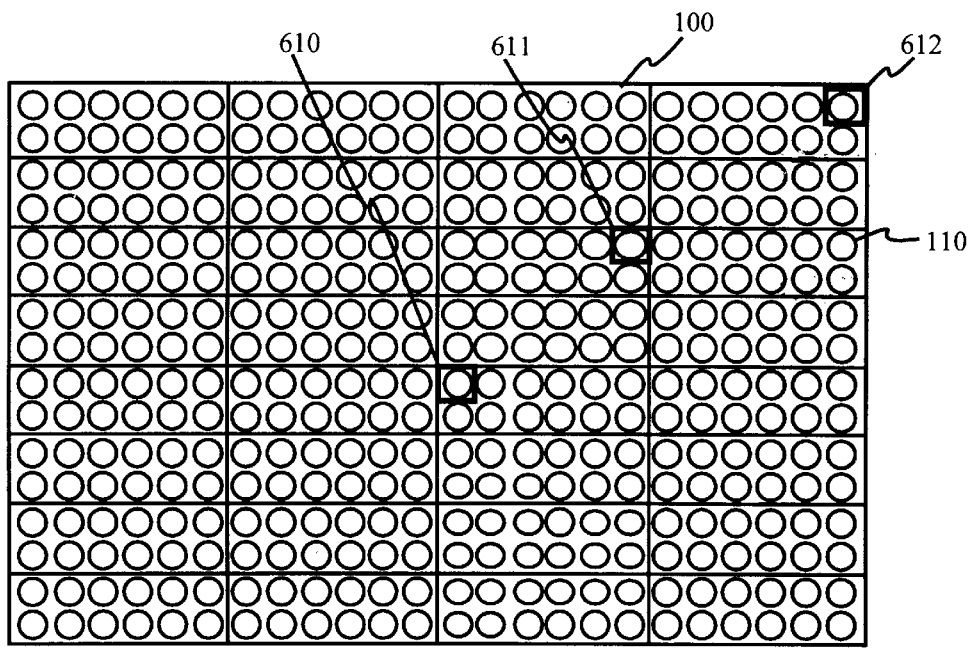
FIGS. 6a–6d illustrate consistent separation of particles across the container in accordance with one embodiment of the invention.

FIGS. 6a–6d illustrate consistent separation of particles across the container in accordance with one embodiment of the invention. Shown in FIG. 6a is the 384-well micro-plate with the arrangement of a number of magnets 310 with their poles 410 in an alternating pattern (shown in FIG. 5b). The 384-well micro-plate is filled with a solution 620 containing a mixture of unwanted particles 650 and target particles 630. Additionally, a number of paramagnetic micro-beads (not shown) is introduced into the solution 620. The paramagnetic micro-beads are micro-beads which are magnetically susceptible when magnetic fields are applied, and when the magnetic fields are no longer applied, the paramagnetic micro-beads no longer are magnetically susceptible.

The paramagnetic micro-beads are coated with a chemical specific substance that will chemically bond with the target particles 630. The application of the magnetic field from the magnets proximate the micro-plate 100 attracts the micro-beads with the bonded target particles 630 towards the magnets 310 of the wells, and the target particles 630 are separated from the unwanted particles 650 within the solution 620. In the illustrated embodiment, the magnets 310 are disposed below the micro-plate 100, and the micro-beads with the bonded target particles 630 are attracted towards the bottom surface of the wells. As a result, the micro-beads with the bonded target particles 630 are separated from the unwanted particles 650 in the solution 620.

Figures 6B, 6C, 6D:
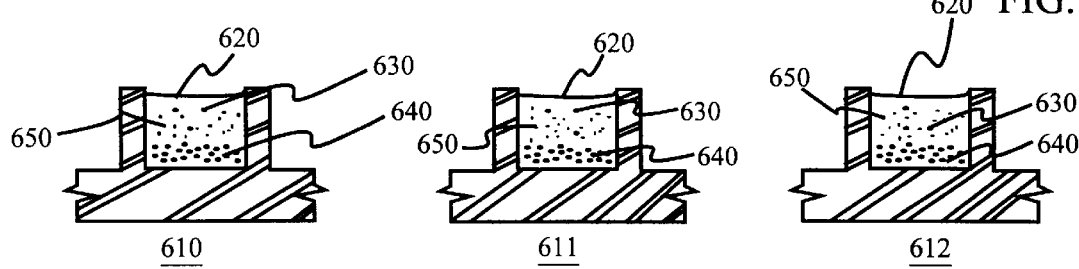

Three wells 610–612 are represented as cross-sectional views illustrating the consistent separation across the micro-plate 100. FIG. 6b illustrates the cross-sectional view of well 610 located towards the center of the micro-plate 100. FIG. 6c illustrates the cross-sectional view of well 611 located a distance away from the center of the micro-plate 100. FIG. 6d illustrates the cross-sectional view of well 612 located at the edge of the micro-plate 100. As shown in FIGS. 6b–6d, the quantity 640 of target particles 630 separated from the solution 620 is substantially similar in the three wells 610–612 from different locations on the micro-plate 100. Additionally, rates at which the separation occurs is substantially similar among the three wells 610–612.

As a result of the arrangement of the magnets 310 with their poles 410 in an alternating repeat pattern, consistent separation of target particles across the container, for example the micro-plate 100, is achieved.

Figure 7A:
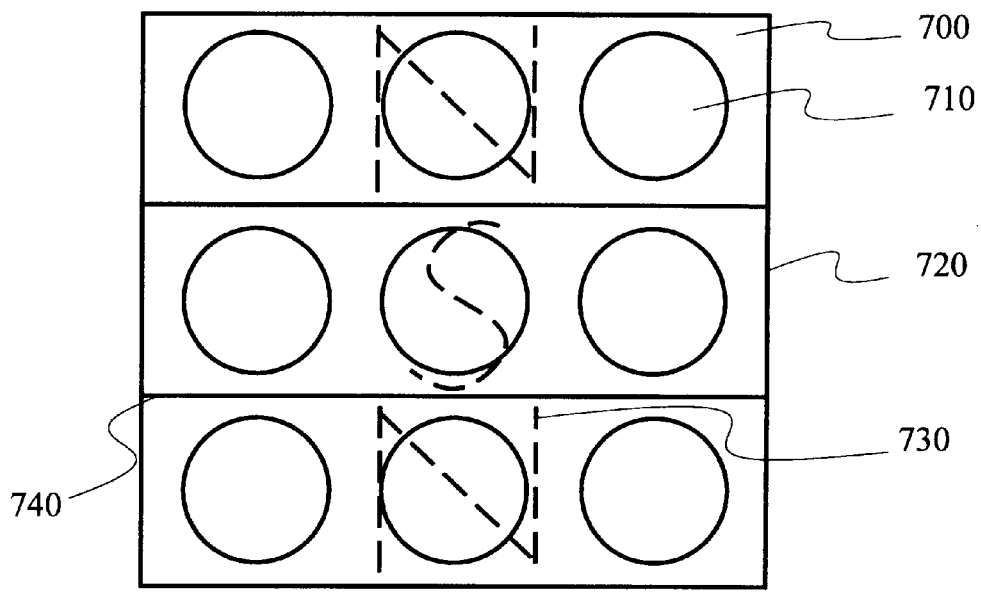
FIGS. 7a and 7b illustrate embodiments of the invention.
Figure 7B:
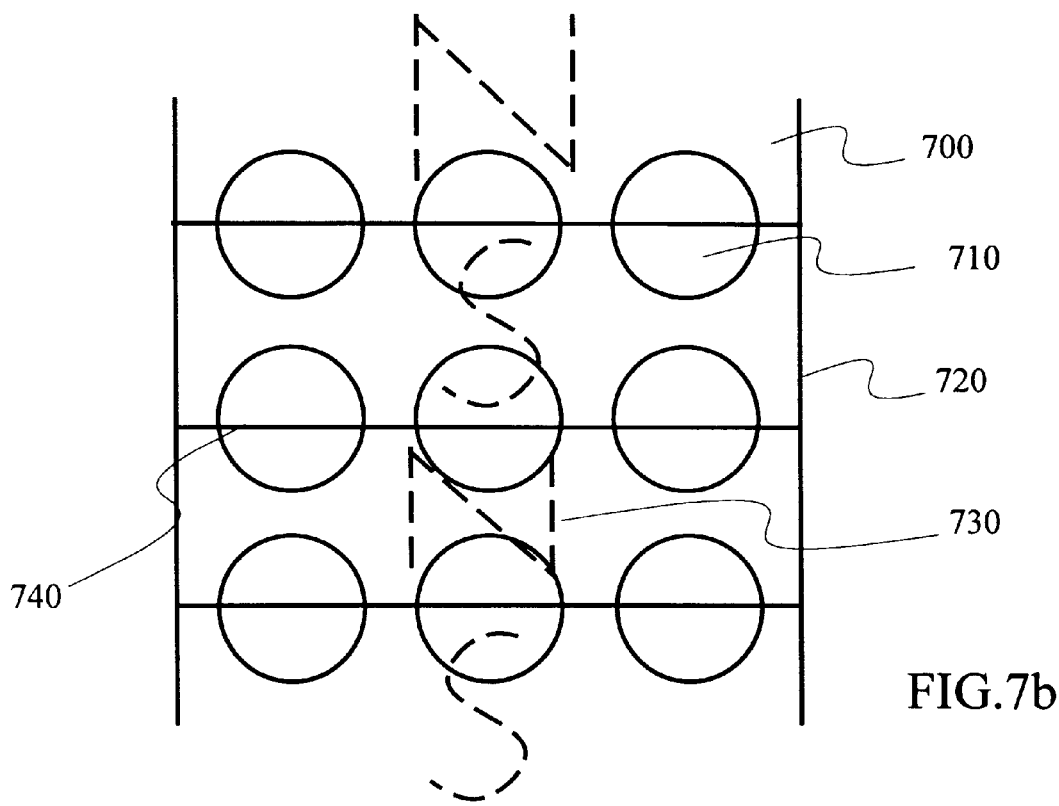

FIGS. 7a and 7b illustrate embodiments of the invention. Shown in FIG. 7a, a container 700 with nine wells 710 is shown, and three magnets 720 are proximate to the container 700, in particular, disposed below the container 700. In FIG. 7a, the wells 710 are placed directly above the poles 730 of the magnets 720. Additionally, as shown in FIG. 7a, the magnets 720 are arranged in a plane to apply magnetic fields on the container 700 for consistent separation of particles across the container 700 in accordance with the invention.

FIG. 7b is one embodiment illustrating the magnets 720 arranged in a plane below the container 700 so that the wells 710 are directly above the borders 740 between the magnets 720 and their respective poles 730. The planar arrangement of magnets 720 shown in FIG. 7b, apply magnetic fields on the container 700 for consistent separation of particles across the container 700.

As shown in FIGS. 7a and 7b, in one embodiment, the magnets 720 may be arranged with their poles 730 below the wells 710 of the container 700, and in one embodiment, the magnets 720 may be arranged with the borders 740 of the poles 730 below the wells 710. However, it should be appreciated by one skilled in the art that the poles 730 and the borders 740 between the magnets 720 and their respective poles may be below any type of container known in the art, such as, but not limited to, a Petri dish utilized for magnetic separation of particles. The number of poles may relate to the number of wells according to Rel. 1. Additionally, the magnets 720 may be proximate to the container 700, such as, but not limited to, sides of the container 700.

As a result, the improved arrangement of the magnets 720, in particular, the poles of the magnets, apply a magnetic field to a container facilitating consistent separation of particles across the container.

Figure 8A:
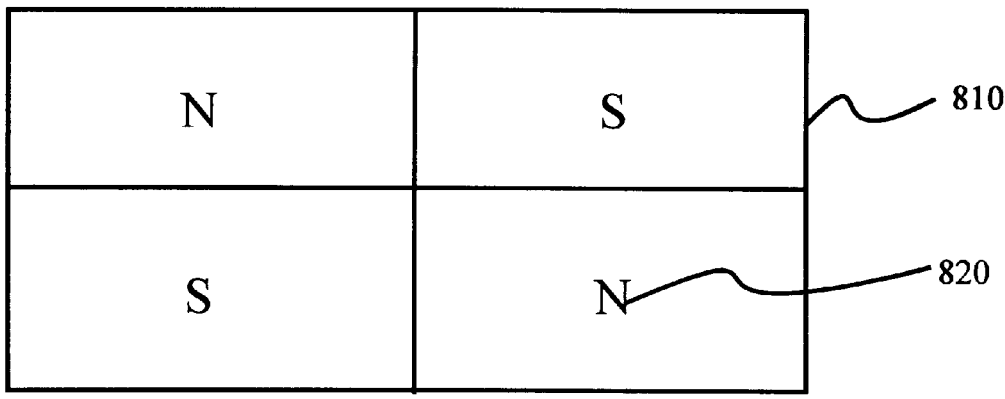
FIGS. 8a–8c illustrate embodiments of the invention with magnets arranged in a plane with the poles of the magnets alternating in a repeat "checkerboard" pattern.
Figure 8B:
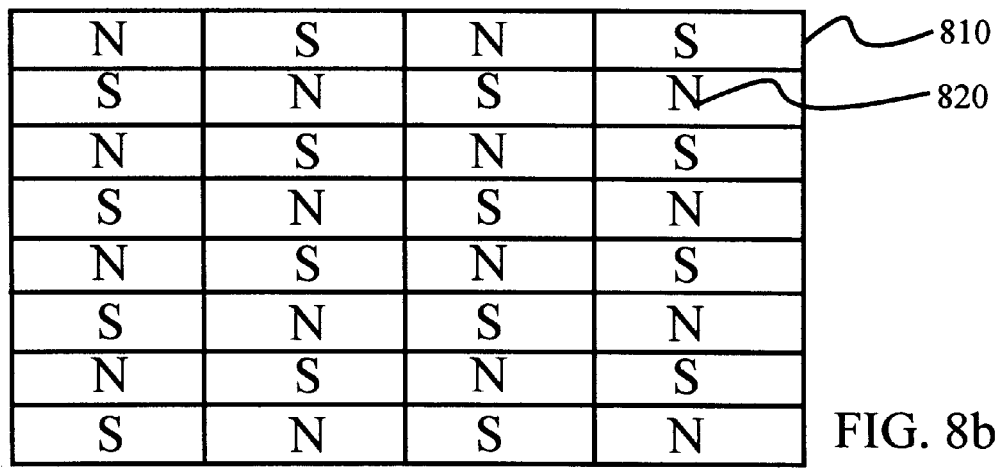
Figure 8C:
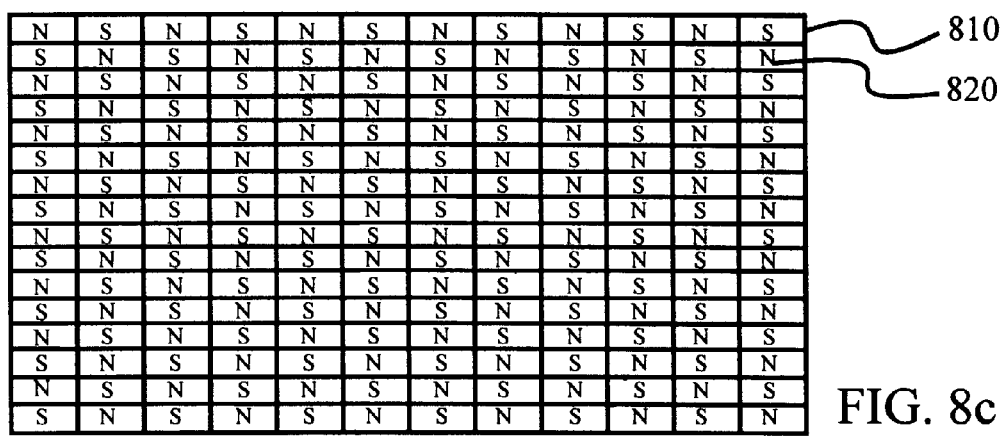

FIGS. 8a–8c illustrate embodiments of the invention with magnets arranged in a plane with the poles of the magnets alternating in a repeat "checkerboard" pattern. As shown in FIGS. 8a–8c, the magnets 810 are arranged in a plane with repeating alternating poles 820 in a "checkerboard" pattern. In accordance with the invention, as the number of magnets 810 and their poles 820 are increased, magnetic fields applied on a container (not shown) above the magnets produce increasing consistency of separation of particles across the container. The magnets arranged in the plane, as shown in FIG. 8c, may be proximate a container such as, but not limited to, 384-well and 1536-well micro-plates. Additionally, the number of poles may relate to the number of wells according to Rel. 1.

Figure 9A:
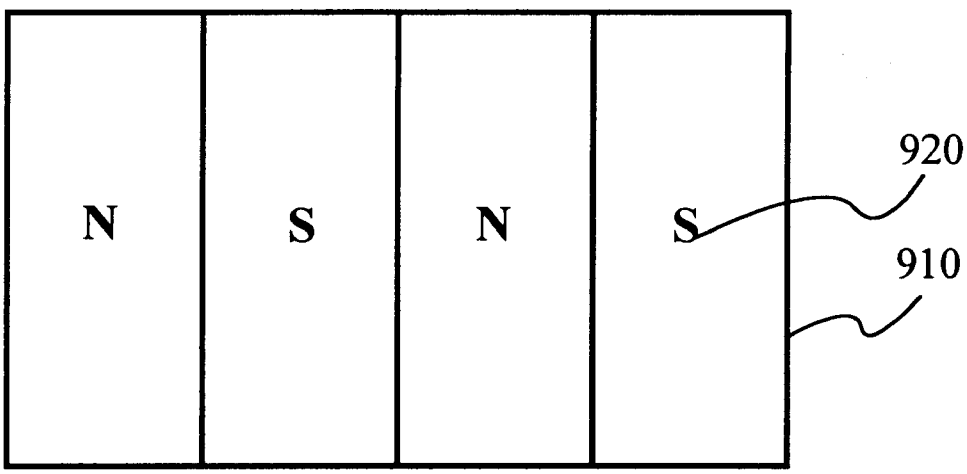
FIGS. 9a and 9b illustrate embodiments of the invention with magnets arranged in a plane with the poles of the magnets alternating in a stripe pattern.
Figure 9B:
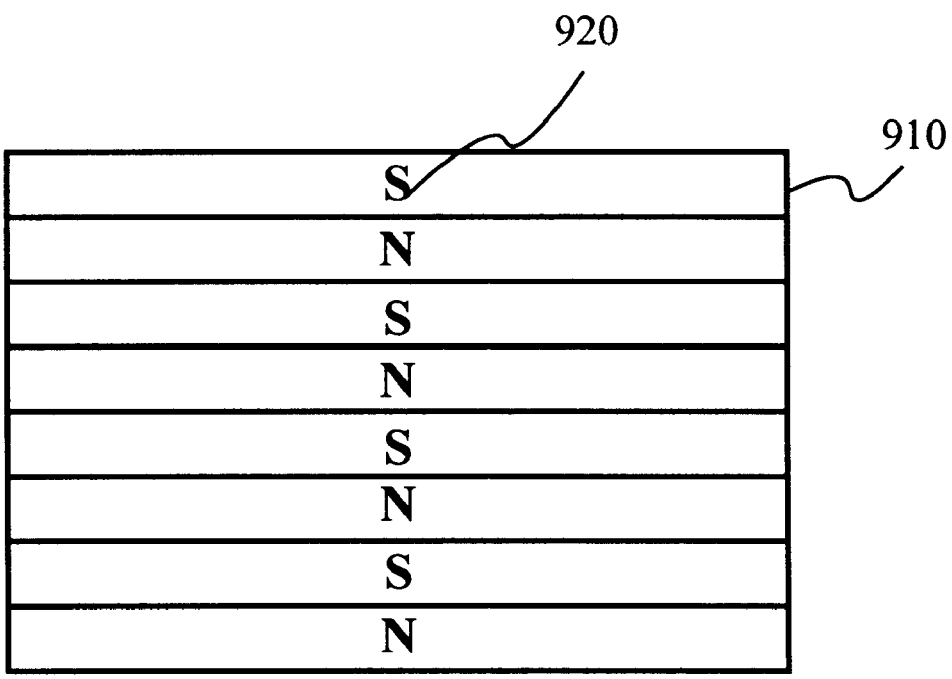

FIGS. 9a and 9b illustrate embodiments of the invention with magnets arranged in a plane with the poles of the magnets alternating in a stripe pattern. As shown in FIGS. 9a and 9b, the magnets 910 are arranged in a plane with repeating alternating poles 920 in a stripe pattern. In accordance with the invention, the magnets 910 and their poles 920 arranged in the plane with the repeating pattern as shown in FIGS. 9a and 9b, apply magnetic fields upon a container (not shown) above the magnets to produce consistency of separation of particles across the container. The magnets arranged in the flat topology shown in FIGS. 9a and 9b may be proximate a container with lower density containers (relatively small number of wells or relatively large spaces between the wells) such as, but not limited to, Petri dishes and tubes. As described above, the number of poles may relate to the number of wells according to Rel. 1.

Figure 10:
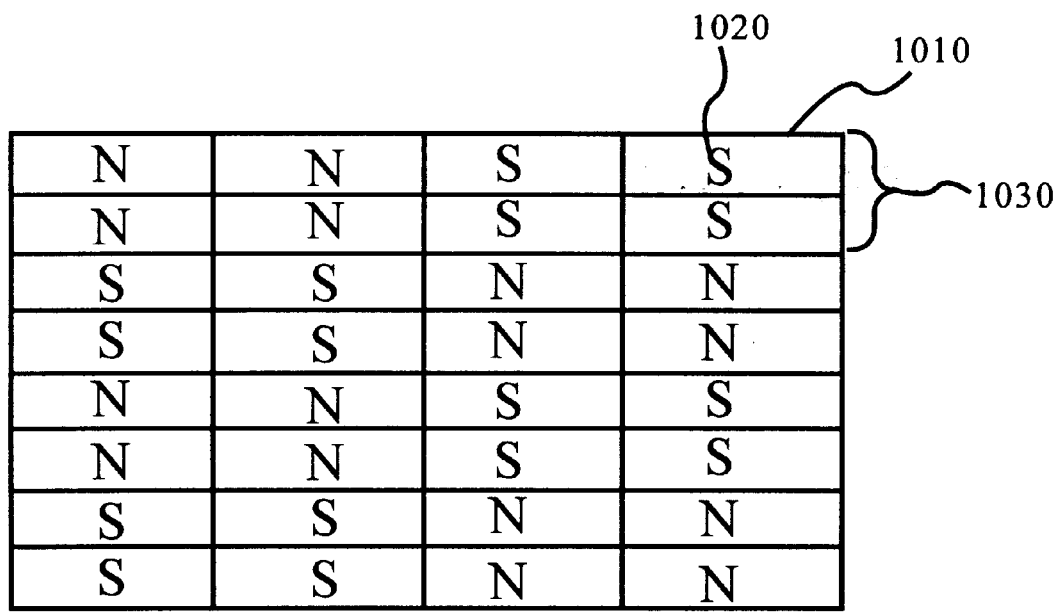
FIG. 10 illustrates one embodiment with magnets arranged in a plane with poles of the magnets alternating in a combined "checkerboard" and stripe pattern.

FIG. 10 illustrates one embodiment with magnets arranged in a plane with poles of the magnets alternating in a combined "checkerboard" and stripe pattern. As shown in FIG. 10, the magnets 1010 are arranged in a plane with repeating alternating poles 1020 in a pattern combining the "checkerboard" pattern (shown in FIGS. 8a–8c) and the stripe pattern (shown in FIGS. 9a and 9b). In FIG. 10, more than one magnet is arranged to produce a single pole 1030.

In accordance with the invention, the magnets 1010 and their poles 1020 are arranged in a plane with repeating alternating poles in a pattern with more than one magnet arranged to produce the single pole 1030 as shown in FIG. 10, apply magnetic fields upon a container (not shown) above the magnets to produce consistency of separation of particles across the container. Again, the number of poles may relate to the number of wells according to Rel. 1.

Figure 11:
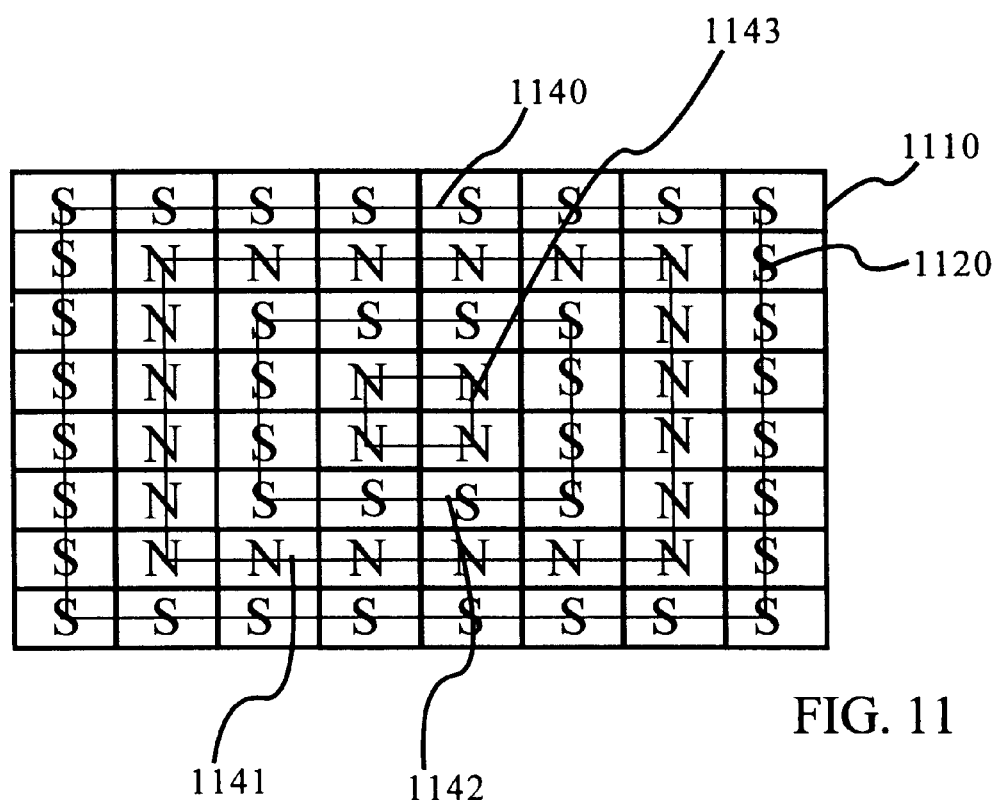
FIG. 11 illustrates one embodiment with the magnets arranged in a plane with the poles of the magnets alternating in a concentric ring pattern.

FIG. 11 illustrates one embodiment with the magnets arranged in a plane with the poles of the magnets alternating in a concentric ring pattern. As shown in FIG. 11, the magnets 1110 are arranged in a plane with repeating alternating poles 1120 in concentric ring patterns 1140–1143. In accordance with the invention, the magnets 1110 and their poles 1120 arranged in a plane with repeating alternating poles in a pattern as concentric rings 1140–1143, as shown in FIG. 11, apply magnetic fields upon a container (not shown) above the magnets to produce consistency of separation of particles across the container. Here again, the number of poles may relate to the number of wells according to Rel. 1.

In general, those skilled in the art will recognize that the invention is not limited by the details described, instead, the invention can be practiced with modifications and alterations within the spirit and scope of the of the appended claims. The description is thus to be regarded as illustrative instead of restrictive on the invention.

Thus, an improved arrangement of magnets, in particular, poles of the magnets, for consistent separation of particles in a solution across a container has been described.

What is claimed is:

1. A magnetic separation apparatus comprising:
   a container to contain a plurality of particles and a plurality of magnetically susceptible particles;
   a plurality of magnets arranged in a plane proximate the container, such that a plurality of magnetic poles of the plurality of magnets apply magnetic fields oriented perpendicular to the plane to facilitate substantially consistent separation of the plurality of magnetically susceptible particles from the plurality of particles across the container.

2. The apparatus of claim 1, wherein the container comprises a multi-well micro-plate.

3. The apparatus of claim 2, wherein the multi-well micro-plate comprises at least one of a 96-well micro-plate, a 384-well micro-plate, and a 1536-well microplate.

4. The apparatus of claim 1, wherein the container comprises at least one of a tube, a vial, a Petri dish, and a bottle.

5. The apparatus of claim 1, wherein the plurality of magnets comprises a plurality of magnets encased within a protective housing.

6. The apparatus of claim 1, wherein the plurality of magnets comprises at least one of a plurality of permanent magnets and a plurality of electromagnets.

7. The apparatus of claim 1, wherein the plurality of poles of the plurality of magnets comprises a plurality of alternating poles arranged in a repeating pattern.

8. A method for magnetic separation comprising:
   providing a container comprising a plurality of particles and a plurality of magnetically susceptible particles;
   arranging a plurality of magnets in a plane proximate the container, such that a plurality of magnetic poles of the plurality of magnets apply magnetic fields oriented perpendicular to the plane to substantially consistently separate the plurality of magnetically susceptible particles from the plurality of particles across the container.

9. The method of claim 8, wherein said providing the container comprises providing a multi-well micro-plate.

10. The method of claim 9, wherein said providing the multi-well micro-plate comprises providing at least one of a 96-well micro-plate, a 384-well micro-plate, and a 1536-well micro-plate.

11. The method of claim 8, wherein said providing the container comprises providing at least one of a tube, a Petri dish, and a bottle.

12. The method of claim 8, wherein said arranging the plurality of magnets comprises encasing the arranged plurality of magnets within a protective housing.

13. The method of claim 8, wherein said arranging the plurality of magnets comprises arranging at least one of a plurality of permanent magnets and a plurality of electromagnets.

14. The method of claim 8, wherein arranging the plurality of magnetic poles comprises arranging a plurality of alternating poles in a repeating pattern.

* * * * *